(12) United States Patent
Laksin

(10) Patent No.: US 6,213,975 B1
(45) Date of Patent: Apr. 10, 2001

(54) INTRA-AORTIC BALLOON CATHETER HAVING AN ULTRA-THIN STRETCH BLOW MOLDED BALLOON MEMBRANE

(75) Inventor: Olga Laksin, Scotch Plains, NJ (US)

(73) Assignee: Datascope Investment Corp., Montvale, NJ (US)

( * ) Notice: Subject to any disclaimer, the term of this patent is extended or adjusted under 35 U.S.C. 154(b) by 0 days.

(21) Appl. No.: 09/545,763

(22) Filed: Apr. 10, 2000

Related U.S. Application Data

(63) Continuation-in-part of application No. 09/188,602, filed on Nov. 9, 1998, now abandoned.

(51) Int. Cl.[7] .................................................. A61M 29/00
(52) U.S. Cl. ...................................... 604/103.13; 604/103
(58) Field of Search .......................... 604/96.01, 103.12, 604/97.01, 99.01, 100.03, 103.06, 103.07, 107, 103

(56) References Cited

U.S. PATENT DOCUMENTS

| | | | |
|---|---|---|---|
| 5,042,985 | * | 8/1991 | Elliott et al. ..................... 604/103.13 |
| 5,316,016 | * | 5/1994 | Adams et al. ............... 604/103.01 X |
| 5,752,522 | * | 5/1998 | Murphy ................................. 600/587 |

* cited by examiner

Primary Examiner—Anhtuan T. Nguyen
(74) Attorney, Agent, or Firm—Abraham Ronai

(57) ABSTRACT

An intra-aortic balloon catheter having an ultra-thin stretch blow molded balloon membrane. The balloon membrane is made from thermoplastic elastomeric and/or semicrystalline materials such as but not limited to polyurethane and polyetheramid.

9 Claims, 3 Drawing Sheets

INTRA-AORTIC BALLOON CATHETER HAVING AN ULTRA-THIN STRETCH BLOW MOLDED BALLOON MEMBRANE

RELATED APPLICATIONS

This application is a continuation-in-part of, and claims priority to, application Ser. No. 09/188,602, filed on Nov. 9, 1998.

BACKGROUND OF THE INVENTION

1. Field of the Invention

The invention relates to an improved intra-aortic balloon catheter. More particularly, the invention relates to an intra-aortic balloon catheter having an ultra-thin stretch blow molded balloon membrane with improved abrasion resistance, fatigue life, and aneurization resistance.

2. Description of the Prior Art

Intra-aortic balloon (IAB) catheters are used in patients with left heart failure to augment the pumping action of the heart. The catheters, approximately 1 meter long, have an inflatable and deflatable balloon at the distal end. The catheter is typically inserted into the femoral artery and moved up the descending thoracic aorta until the distal tip of the balloon is positioned just below or distal to the left subclavian artery. The proximal end of the catheter remains outside of the patient's body. A passageway for inflating and deflating the balloon extends through the catheter and is connected at its proximal end to an external pump. The patient's central aortic pressure is used to time the balloon and the patient's ECG may be used to trigger balloon inflation in synchronous counterpulsation to the patient's heart beat.

Intra-aortic balloon therapy increases coronary artery perfusion, decreases the workload of the left ventricle, and allows healing of the injured myocardium. Ideally, the balloon should be inflating immediately after the aortic valve closes and deflating just prior to the onset of systole. When properly coordinated, the inflation of the balloon raises the patient's diastolic pressure, increasing the oxygen supply to the myocardium; and balloon deflation just prior to the onset of systole lowers the patient's diastolic pressure, reducing myocardial oxygen demand.

Intra-aortic balloon catheters may also have a central passageway or lumen which can be used to measure aortic pressure. In this dual lumen construction, the central lumen may also be used to accommodate a guide wire to facilitate placement of the catheter and to infuse fluids, or to do blood sampling.

Typical dual lumen intra-aortic balloon catheters have an outer, flexible, plastic tube, which serves as the inflating and deflating gas passageway, and a central tube therethrough formed of plastic tubing, stainless steel tubing, or wire coil embedded in plastic tubing. A polyurethane compound is used to form the balloon.

All IAB catheters have two opposing design considerations. On the one hand, it is desirable to make the outer diameter of the entire catheter as small as possible: to facilitate insertion of the catheter into the aorta, maximizing blood flow past the inserted catheter, and to allow for the use of a smaller sheath to further maximize distal flow. On the other hand, however, it is desirable to make the inner diameter of the outer tube as large as possible because a large gas path area is required to accomplish the rapid inflation and deflation of the balloon. As a result of these opposing design considerations there is a need for a smaller catheter with a larger gas path area.

One method of making the outer diameter of the wrapped balloon portion of the catheter as small as possible is to wrap the balloon in its deflated state as tightly as possible around the inner tube. Wrapping the balloon tightly, however, has posed a number of difficulties. First, it is difficult to wrap the balloon tightly because of the friction between contacting surfaces of the balloon. Second, contacting surfaces of a tightly wrapped balloon may stick upon initial inflation. Datascope Investment Corp.'s co-pending application Ser. No. 08/958,004, filed on Oct. 27, 1997, herein incorporated by reference in its entirety, discloses a lubricous coating for the balloon membrane which solves the above mentioned problems. The coating allows the balloon membrane to be wrapped tightly more easily and prevents sticking of the balloon membrane upon initial inflation.

A second method of making the outer diameter of the wrapped balloon portion of the catheter as small as possible is to decrease the size of the inner tube. Datascope Investment Corp.'s co-pending application Ser. No. 08/958,004 also discloses an intra-aortic balloon catheter with an inner tube having a smaller diameter only in the portion enveloped by the balloon membrane.

Although the above two methods have substantially reduced the overall insertion size of the intra-aortic balloon catheter the need still exists for greater size reduction. Furthermore, the need also exists for a balloon membrane with improved abrasion resistance, fatigue life, and aneurization resistance. Currently, the method of manufacturing polyurethane balloon membranes is solvent casting. This casting method does not provide the formed membrane with ideal physical and mechanical properties. A solvent caste membrane with the basic mechanical properties necessary for balloon pumping, typically has a single wall thickness of 4 to 6 mils (a mil is equal to one thousandth of an inch) which leads to a relatively large wrapped diameter of the balloon membrane. A thin solvent caste polyurethane membrane is capable of being manufactured, however, such a membrane does not demonstrate the required abrasion resistance and fatigue life. Therefore, the need exists for an improved method of making a balloon membrane which will allow for a balloon membrane having a reduced thickness, and at the same, having improved mechanical properties, including an improved abrasion resistance, fatigue life, and aneurization resistance.

The present invention comprises an intra-aortic balloon catheter having a stretch blow molded balloon membrane. The balloon membrane is made from thermoplastic elastomeric and/or semicrystalline materials such as but not limited to polyurethane and polyetheramid. As discussed above, intra-aortic balloon membranes are generally solvent cast.

The process of stretch blow molding catheter balloon membranes is known in the art. However, intra-aortic balloons have been traditionally made by solvent casting because intra-aortic balloon membranes require special characteristics: they must be substantially nondistensible and have high abrasion resistance, fatigue life, and aneurization resistance. Stretch blow molding has been traditionally used for angioplasty balloon membranes. These balloons are generally made from PET, Nylon, or PEBAX materials. These materials achieve their high strength at least partially because of the crystallization formed in their microstructure during the initial stretching step of the tube and as a result of quickly cooling the tube to a temperature below the crystallization temperature of the tube material. Crystallization of the microstructure increases the strength of the balloon membrane, however, as the inventors of the present invention have discovered, it has a negative effect on the abrasion resistance and fatigue life of the balloon membrane. Given that angioplasty balloon/PTCA therapy is a short duration therapy, crystallization is generally not a problem. Actually, it is quite useful given that it enhances the strength of the balloon material. Intra-aortic balloon therapy, on the other hand, involves repetitive inflation and deflation of the balloon membrane over a longer period of time. Accordingly, it is known in the art that stretch blow molded balloons are not appropriate for intra-aortic balloon membranes, which require high strength as well as high abrasion resistance and fatigue life.

The present invention overcomes the above described obstacle by relying on the increased strength of polyurethane resulting from the high orientation and molecular interaction of the polyurethane molecules along the longitudinal axis of the tube. Said orientation results from stretching the tube until substantially all stretchability is removed. Polyurethane, and the other materials listed in the present application, do not exhibit significant stress induced crystallization upon stretching. Accordingly, the inventors of the present invention have discovered a means to create a balloon membrane strong enough to endure intra-aortic balloon pumping therapy without creating crystallization microstructure, which they have discovered, is detrimental to the abrasion resistance and fatigue life of the balloon membrane.

U.S. Pat. No. 5,370,618 to Leonhardt discloses a pulmonary artery balloon catheter comprising a catheter terminating in a blow molded polyurethane balloon membrane. Pulmonary artery catheters are generally used for blood pressure measurements. Upon insertion and placement of the catheter the balloon membrane is inflated, occluding the housing blood vessel, so as to create a measurable pressure differential on either side of the balloon membrane. In order to achieve complete occlusion of the housing blood vessel the pulmonary artery catheter balloon membrane is elastic so as to allow expansion of the membrane. This is in contrast to the balloon membrane of the present invention which is stretch blow molded and is specifically manufactured to substantially eliminate distensibility in the final product.

SUMMARY OF THE INVENTION

Accordingly, it is an object of the invention to produce an ultra-thin intra-aortic balloon membrane with superior abrasion resistance and fatigue life.

It is another object of the invention to produce a method for manufacturing said ultra-thin intra-aortic balloon membrane.

The invention is an intra-aortic balloon catheter having an ultra-thin stretch blow molded balloon membrane. The balloon membrane is made from thermoplastic elastomeric and/or semicrystalline materials such as but not limited to polyurethane and polyetheramid.

To the accomplishment of the above and related objects the invention may be embodied in the form illustrated in the accompanying drawings. Attention is called to the fact, however, that the drawings are illustrative only. Variations are contemplated as being part of the invention, limited only by the scope of the claims.

BRIEF DESCRIPTION OF THE DRAWINGS

In the drawings, like elements are depicted by like reference numerals. The drawings are briefly described as follows.

DETAILED DESCRIPTION OF THE PREFERRED EMBODIMENTS

Figure 1:
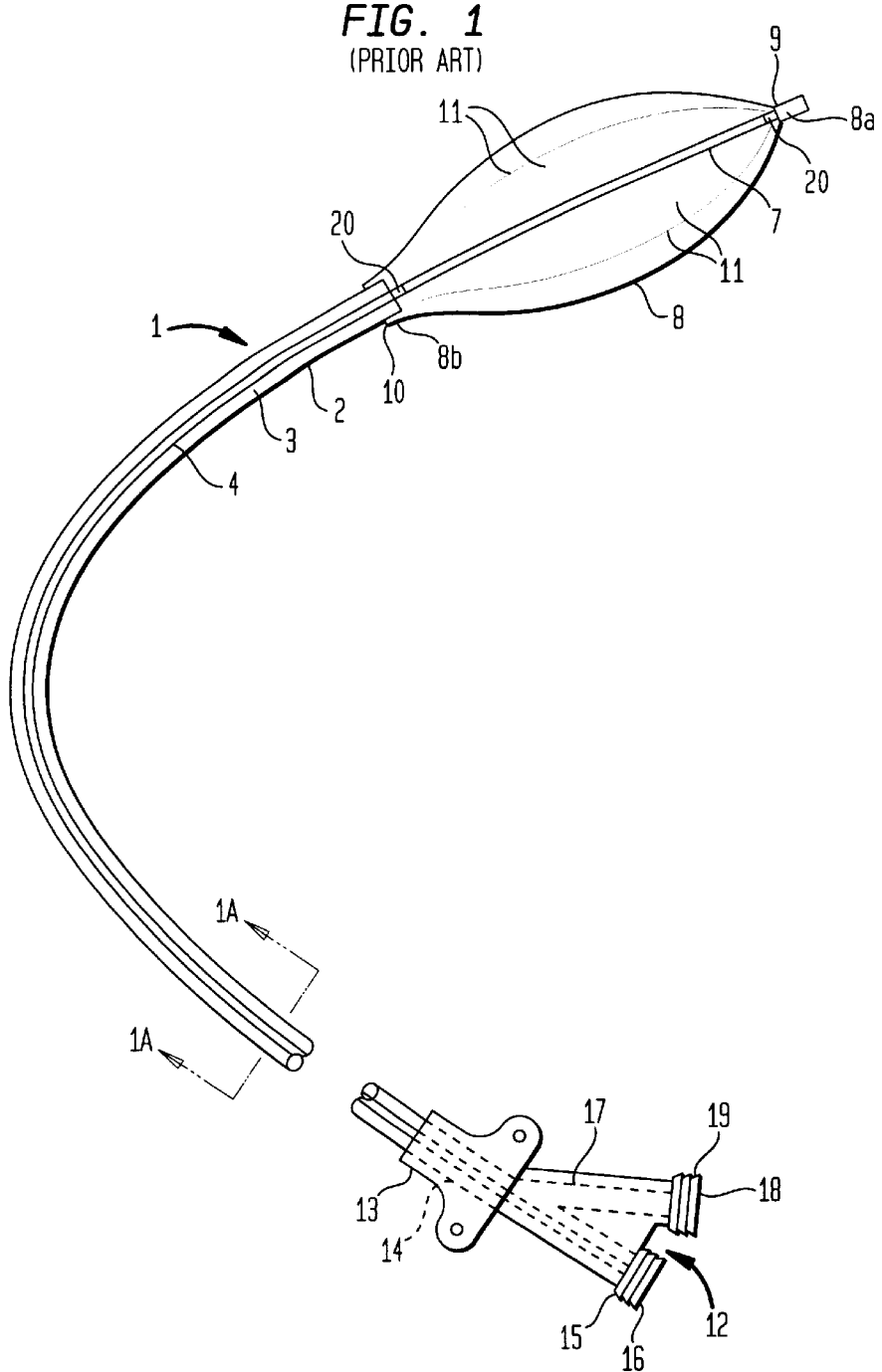
FIG. 1 is longitudinal cross section of a prior art intra-aortic balloon catheter.
Figure 1A:
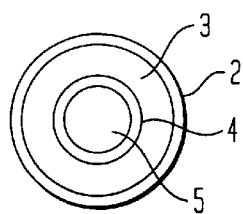
FIG. 1A is a transverse cross section of the prior art intra-aortic balloon catheter taken along line 1A—1A.

The general structure of an intra-aortic balloon catheter is best described in relation to FIGS. 1 and 1A which illustrate a dual-lumen prior art intra-aortic balloon catheter. The catheter 1 is constructed of a plastic outer tube 2 forming a gas passageway lumen 3; and another plastic central tube 4 disposed within outer tube 2 and creating a central passageway or lumen 5 as may best be seen in FIG. 1A.

A balloon 8 is disposed at the distal end of the catheter 1.

The distal portion 7 of the central tube 4 extends beyond the distal end 10 of outer tube 2. The distal end 8A of the balloon 8 is attached to a tip 9 formed on the distal end 7 of central tube 4. The proximal end 8B of the balloon 8 is attached, by means of a lap joint, to the distal end 10 of the outer tube 2. The distal portion 7 of the central tube 4 supports the balloon 8. Said distal portion 7 must have sufficient strength to prevent inversion of the balloon 8 as it inflates and deflates under aortic pressure, but at the same time, be flexible enough to be safely inserted through an introducer sheath, moved through the arterial tree, and maintained in the thoracic aorta.

The balloon 8 is formed of a nonthrombogenic flexible material, such as polyurethane, and may have folds 11 formed as a result of wrapping the balloon 8 about the central tube 4 to ease insertion of the catheter 1. The balloon 8 has a single wall thickness of between 4 to 6 mils. Radio-opaque bands 20 at the distal end of the catheter 1 aid in positioning the balloon 8 in the descending aorta.

Inflation and deflation of the balloon 8 is accomplished through the gas passageway lumen 3. The central passageway or lumen 5 can accommodate a guide wire for placement or repositioning of the catheter 1. When the guide wire is not disposed in the central passageway or lumen 5, the central passageway or lumen 5 may be used for measuring blood pressure in the descending aorta. This pressure measurement may be used to coordinate the inflation and deflation of the balloon 8 with the pumping of the heart, however, use of the patient's ECG is preferred. Additionally, the central passageway or lumen 5 may be used to infuse liquids into the descending aorta, or to sample blood.

At the proximal end 12 of the catheter 1 a hub 13 is formed on the proximal end 14 of the outer tube 2. The central passageway or lumen 5 extends through the hub 13 and a connector 16 is provided at the proximal end 15 (or exit) of the central passageway or lumen 5. Measurement of aortic pressure and blood sampling may be done through the proximal end 15 of the central passageway or lumen 5.

The proximal end 18 of the gas passageway or lumen 3 exits through a side arm 17 of the hub 13 on which is provided a connector 19. The proximal end 18 of the gas passageway or lumen 3 may be connected to an intra-aortic balloon pump.

Figure 2:
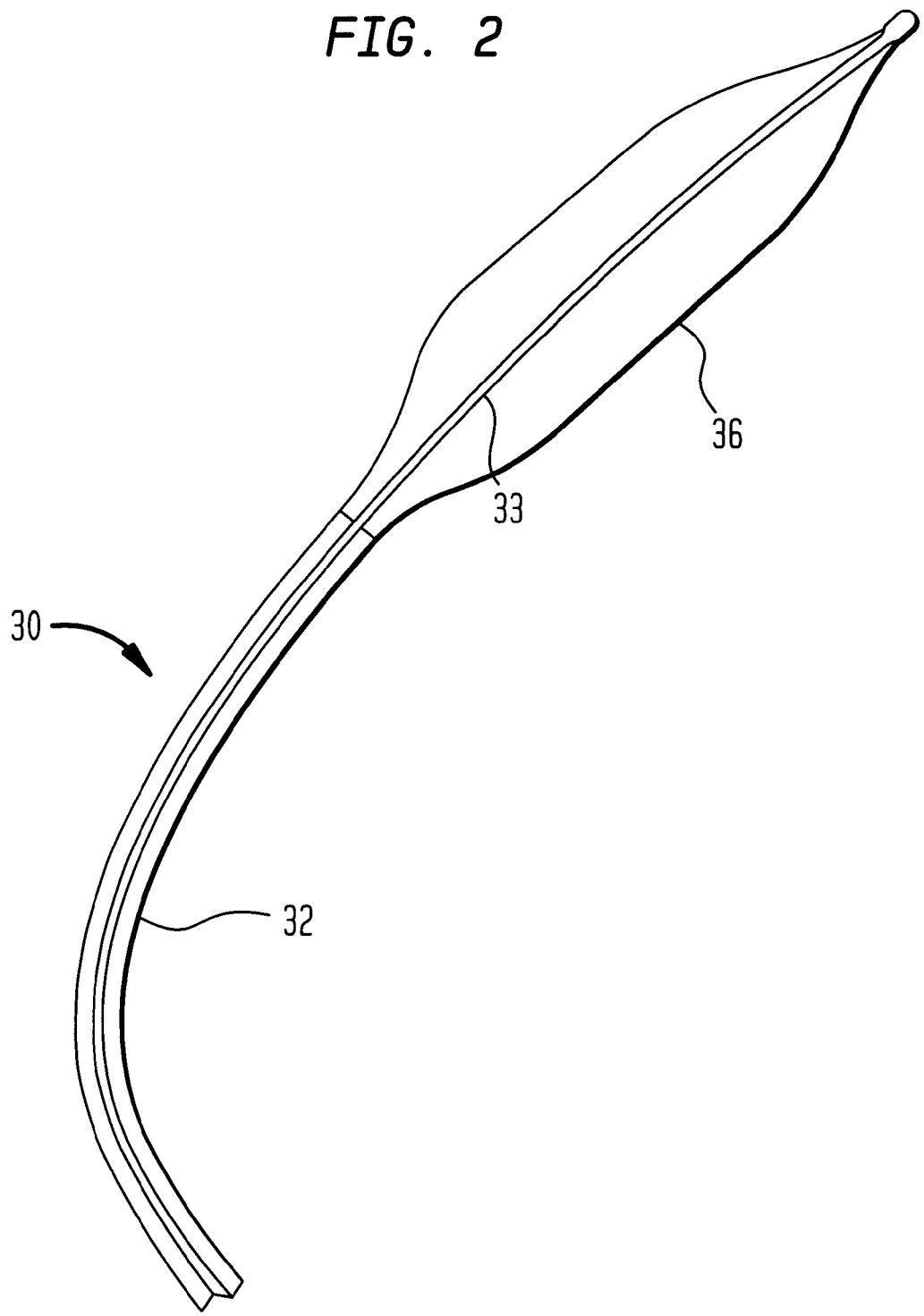
FIG. 2 is a longitudinal cross sectional view of a distal portion of the improved intra-aortic balloon catheter.

The present invention comprises an intra-aortic balloon catheter having an ultra-thin stretch blow molded balloon membrane. FIG. 2 illustrates a longitudinal cross sectional view of a distal portion of an improved intra-aortic balloon catheter 30 of the present invention comprising an outer tube 32, an inner tube 33, a tip 34, and an ultra-thin polyurethane balloon membrane 36. The tip 34 is connected to a distal end of the balloon membrane 36. A distal end of the outer tube 32 is seamlessly welded to a proximal end of the balloon membrane 36. The balloon membrane 36 has a single wall thickness of between 1 to 2 mils.

The balloon membrane 36 may be made from a variety of thermoplastic elastomeric and/or semicrystalline materials including but not limited to polyurethane and polyetheramid (known by its trade name as PEBAX, produced by ELF-Atochem of Europe).

Another feature of the invention involves the attachment of the outer tube 32 and the balloon membrane 36. The distal end of the outer tube 32 is seamlessly welded to the proximal end of the balloon membrane 36. The distal end of the outer tube 32 has the same inner and outer diameters as the proximal end of the balloon membrane 36, thus providing a smooth transition between the two parts without a constriction of the gas path. This is in contrast to the prior art catheter 1 of FIG. 2 in which the proximal end of the balloon 8 and the distal end of the catheter 1 are attached by means of a lap joint. The lap joint is generally compressed during the manufacturing process in order to assure that the outer diameter of the lap joint matches that of the outer tube 2. Compression of the lap joint area leads to a restriction in the gas flow path. The present invention avoids this restriction through the use of a seamless weld.

Figure 3:
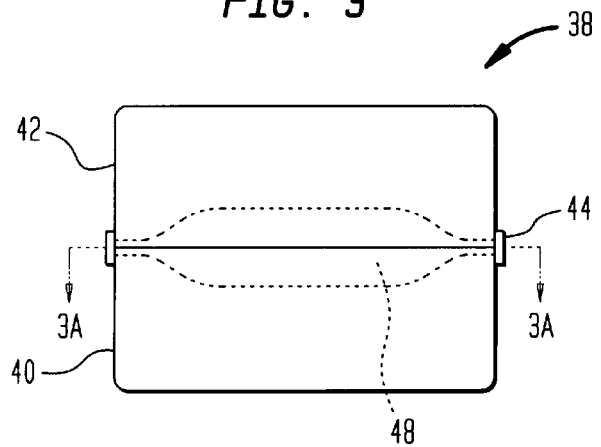
FIG. 3 is a side view of a mold having a balloon shaped cavity used to manufacture the balloon membrane.

FIG. 3 illustrates a side view of a mold 38 with tube clamps 44 on both sides for securing a tube 46 having ends 50 to the mold 38. The mold 38 has a first half 40 and a second half 42 and is utilized in the manufacturing of the ultra-thin balloon membrane 36 to assure the required profile of said balloon membrane 36. The first half of the mold 40 and the second half of the mold 42 together define a balloon shaped cavity 48 illustrated in FIG. 3 as a shadowed segmented line.

Figure 4:
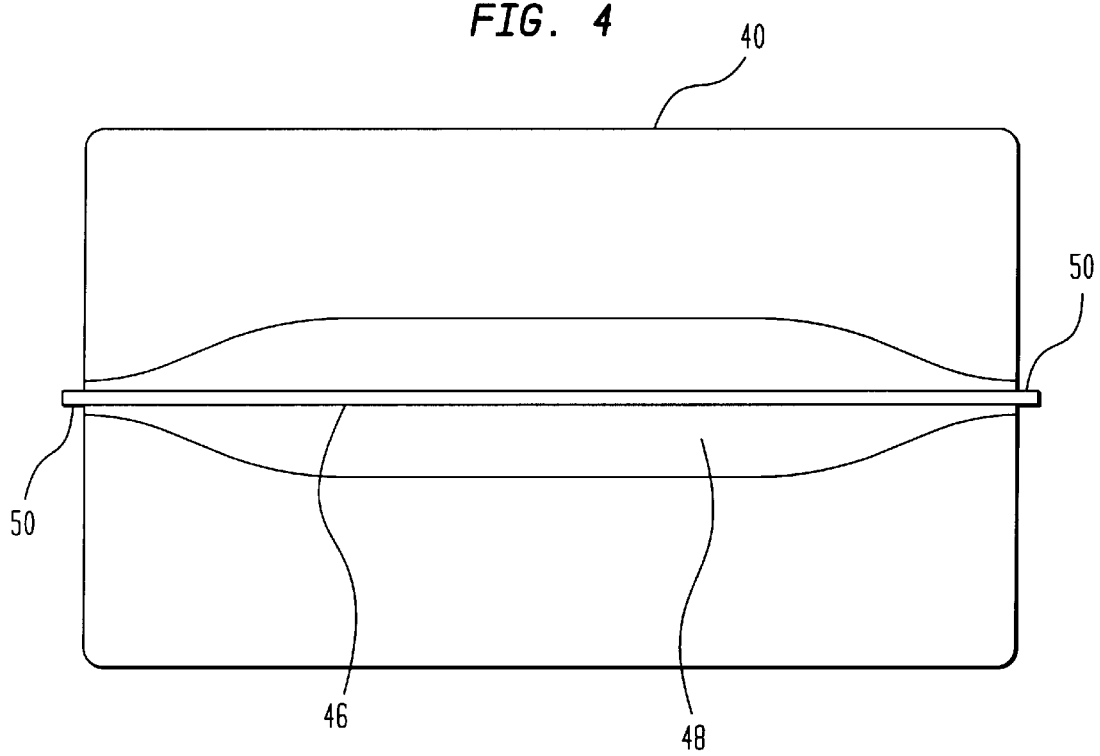
FIG. 4 is a top view of the first half of the mold containing and securing a stretched tube used as a preform to create the balloon membrane.

The manufacturing process of the balloon membrane 36 comprises the following steps. First, a tube 46, as illustrated in FIG. 4, is stretched to the desired length of the balloon membrane 36. In the preferred embodiment, and in this example, the tube 46 is 8 inches long, has a wall thickness of 0.02 inches, and is made from polyurethane; however, the tube 46 may be of a different size and may made from other thermoplastic elastomeric and/or semicrystalline materials or other materials that do not display stress induced crystallization or a combination of such materials.

FIG. 4 illustrates a top plain view of the first half 40 of the mold 38 which is identical to a view of the mold 38 taken along lines 3A—3A. The ends 50 of the tube 46 are secured by means of the clamps 44 (not shown in FIG. 4 for clarity) to opposite sides of the mold 38. The second half 42 of the mold 38, as illustrated in FIG. 3, is attached to the first half of the mold enclosing the stretched tube 46 in the balloon shaped cavity 48.

Stretching the tube 46, approximately two times its original length, prior to blowing orientates the polyurethane molecules along the longitudinal axis of the tube and substantially eliminates any further stretchability of the balloon membrane 36, at internal pressures of two to four psi, by achieving a high molecular orientation and interaction. Note that this orientation and molecular interaction is achieved without significant crystallization; this is important to assure improved abrasion resistance and fatigue life. Significant crystallization is defined as any amount of crystallization which negatively affects the abrasion resistance and fatigue life of the balloon membrane. Polyurethane and polyetheramid, and other thermoplastic elastomeric and/or semicrystalline materials, do not exhibit stress induced crystallization. This is in contrast to the materials traditionally used for stretch blow molded angioplasty balloon catheter membranes which on average have approximately 30% crystallization.

The stretching step assures the substantial nondistensibility of the final balloon membrane 36 under balloon inflation pressures of approximately 2–4 psi. This is in contrast to the pulmonary artery balloon catheter, discussed above, whose polyurethane balloon membrane is specifically designed to be distensible so as to allow the membrane to expand, and thereby, occlude the blood vessel in which blood pressure is being measured.

The next manufacturing step involves filling the tube 46 with a gas at approximately 150 psi, i.e. blowing the tube 46. The amount of pressure applied depends on the grade of polyurethane: harder materials require higher pressure. In all cases, however, the pressure must be sufficient to force the tube 46 to take on the shape of the mold cavity 48. The tube 46 is then heated above the tube melting temperature while maintaining a pressure of 30–40 psi in the tube 46. The final step involves quickly cooling the ballooned tube 46, to a temperature above the crystallization temperature of the tube 46, while maintaining a pressure of approximately 80 psi in the tube 46. The final thickness of the ballooned tube 46, approximately 0.002 inches, is significantly thinner than the prior art thickness of approximately 0.004–0.006 inches.

It should be noted that the above detailed manufacturing process is merely an illustrative example and will vary for different sized tubes and for tubes made of different materials. Manufacturing variables include tube material, tube length, tube thickness, tube diameter, the required pressure for blowing, the temperature for heating and cooling of the tube, and the amount of pressure maintained in the tube while heating and cooling the tube.

It should further be noted that balloon membrane of the present invention may be used with any variation of intra-aortic balloon catheters, including an intra-aortic balloon catheter having a co-lumen catheter, i.e. the inner lumen attached to or embedded in the catheter wall, or with any balloon catheter that requires a balloon membrane with improved abrasion resistance and fatigue life.

What is claimed is:

1. An intra-aortic balloon catheter comprising an outer tube with proximal and distal ends, and a stretch blow molded balloon membrane with a proximal end connected to the distal end of the outer tube, said balloon membrane having been stretched without creating significant crystallization to substantially eliminate stretchability under balloon inflation pressures of approximately 2–4 psi.

2. The intra-aortic balloon catheter as claimed in claim 1 wherein the balloon membrane is at least partially composed of a thermoplastic elastomeric material.

3. The intra-aortic balloon catheter as claimed in claim 1 wherein the balloon membrane is at least partially composed of a semicrystalline material.

4. The intra-aortic balloon catheter as claimed in claim 1 wherein the balloon membrane is at least partially composed of a thermoplastic elastomeric semicrystalline material.

5. The intra-aortic balloon catheter as claimed in claim 1 wherein the balloon membrane is at least partially composed of polyurethane.

6. The intra-aortic balloon catheter as claimed in claim 1 wherein the balloon membrane is at least partially composed of polyetheramid.

7. The intra-aortic balloon catheter as claimed in claim 2 wherein the balloon membrane is made from polyurethane.

8. The intra-aortic balloon catheter as claimed in claim 1 wherein the intra-aortic balloon catheter further comprises an inner tube at least partially disposed within an outer surface of the outer tube, a distal end of said inner tube being connected to a distal end of the balloon membrane.

9. An intra-aortic balloon catheter comprising an outer tube with proximal and distal ends, and a stretch blow molded polyurethane balloon membrane with a proximal end connected to the distal end of the outer tube, said balloon membrane having been stretched without creating significant crystallization to substantially eliminate stretchability under balloon inflation pressures of approximately 2–4 psi.

* * * * *